(12) United States Patent
Brahms et al.

(10) Patent No.: US 6,403,652 B1
(45) Date of Patent: Jun. 11, 2002

(54) METHOD AND COMPOSITION

(75) Inventors: John Brahms, Piscataway; Bruce Nascimbeni, Millstone; Sukhvinder Sandhu, East Brunswick, all of NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 09/608,366

(22) Filed: Jun. 30, 2000

(51) Int. Cl.[7] ............... A61K 31/045; A61K 31/05
(52) U.S. Cl. ............... 514/728; 514/731; 514/734; 514/736
(58) Field of Search ............... 514/728, 736, 514/734, 731

(56) References Cited

U.S. PATENT DOCUMENTS

| | | | |
|---|---|---|---|
| 3,884,906 A | 5/1975 | Van der Meer et al. | 260/211 |
| 4,131,672 A | 12/1978 | Huffman | 424/246 |
| 4,175,125 A | 11/1979 | Huffman | 424/246 |
| 4,447,427 A | 5/1984 | Klayman et al. | 424/244 |
| 4,625,041 A | 11/1986 | Celmer et al. | 549/343 |
| 4,816,441 A | 3/1989 | Zeuthen et al. | 514/12 |
| 5,043,334 A | 8/1991 | Bell et al. | 514/207 |
| 5,208,257 A | 5/1993 | Kabara | 514/552 |
| 5,334,613 A | 8/1994 | Kojiri et al. | 514/452 |
| 5,399,723 A | 3/1995 | Iinuma et al. | 549/403 |
| 5,602,183 A | 2/1997 | Martin et al. | 514/724 |
| 5,620,969 A | 4/1997 | Bronson et al. | 514/203 |
| 5,635,184 A | 6/1997 | Camano | 424/195 |
| 5,641,503 A | 6/1997 | Brown-Skrobot | 424/431 |
| 5,658,956 A | 8/1997 | Martin et al. | 514/724 |
| 5,668,290 A | 9/1997 | Bronson et al. | 546/298 |
| 5,703,040 A | 12/1997 | Iandolo et al. | 514/2 |
| 5,723,500 A * | 3/1998 | Stringer et al. | 514/736 |
| 5,756,120 A | 5/1998 | Hersch et al. | 424/450 |
| 5,759,571 A | 6/1998 | Hersch et al. | 424/450 |
| 5,824,698 A | 10/1998 | Hasler et al. | 514/394 |
| 5,856,364 A | 1/1999 | Martin | 514/724 |
| 5,863,938 A | 1/1999 | Martin | 514/461 |
| 5,866,539 A | 2/1999 | Blackburn et al. | 514/9 |
| 5,888,524 A | 3/1999 | Cole | 424/402 |
| 5,998,487 A * | 12/1999 | Brahms et al. | 514/736 |

FOREIGN PATENT DOCUMENTS

| | | | |
|---|---|---|---|
| EP | 0463780 A2 | 1/1992 | A61K/7/06 |
| EP | 0738509 A2 | 10/1996 | A61K/7/48 |
| EP | WO97/32568 | 9/1997 | A61K/7/50 |
| WO | 97/10800 | * 3/1997 | |
| WO | 99/51559 | * 10/1999 | |

OTHER PUBLICATIONS

Biological Activity of Essential Oils and Their Constituents by Tetsuo Nakatsu, Andrew T.. Lupo Jr., John W. Chinn Jr., and Raphael K.L. Kang, Takasago Institute for Interdisciplinary Science, 4 Volvo Dr., Rockleigh, NJ 07647 U.S.A.

* cited by examiner

*Primary Examiner*—Kevin E. Weddington
(74) *Attorney, Agent, or Firm*—Martin B. Barancik

(57) ABSTRACT

A method for inhibiting methicillin drug resistant bacteria using a phenolic compound.

10 Claims, No Drawings

METHOD AND COMPOSITION

FIELD OF THE INVENTION

The indication and inhibition of disease causing bacteria has been one of the most significant events of the twentieth century. Diseases such as tuberculosis, pneumonia, and typhoid which were primary killers of people in the early twentieth century are presently far less significant diseases than they once were. One of the chief reasons for this phenomenon is the successful treatment of bacteria induced illness through the use of antimicrobial drugs such as antibiotics, semi synthetic antibiotics, and chemically synthesized compounds. However, bacteria have developed varying degrees of resistance to some or virtually all of these drugs. These "superbugs" can bring about a disease in a human which can result in death. Although such drug resistant bacteria can be found almost anywhere, they are a particular problem in hospitals, a locus where antibacterial drugs are used in high frequency. It has been recently reported that about 2 million hospital patients per year become infected, resulting in about 60,000 to 80,000 deaths. Staphylococcus bacteria, particularly staphaureus are the leading cause of hospital borne infection. Health care professionals are increasingly concerned about this issue. Greater focus is on the discovery of new chemical entities which will be successful in combating such bacteria.

It has now been discovered that certain types of compounds known to be effective antibacterial materials for many years are also effective against drug resistant bacteria. These compounds, particularly alkyl phenols, are effective against antibiotic resistant *staphylococcus aureas* (*S. aureas*). Specifically, these alkyl phenols are highly effective against methicillin resistant *S. aureas*.

SUMMARY OF THE INVENTION

In accordance with the invention, there is a method for inhibiting drug resistant bacteria which comprises administering to a host or surface in need of said treatment a composition comprising an antibacterially effective amount against drug resistant bacteria of a compound or a mixture of compounds of the formula:

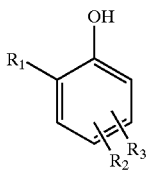

wherein
$R_1$ is selected from the group consisting of branched alkyl of four to about twenty carbon atoms, cycloalkyl of from four to about eight carbon atoms, mono cycloalkyl substituted alkyl of from four to about twelve carbon atoms where cycloalkyl is about four to about eight carbon atoms, and mono to tetra alkyl substituted cycloalkyl of from four to about eight carbon atoms wherein alkyl is one to about four carbon atoms;

$R_2$ is at the 4 or 5 position and is selected from the group consisting of branched alkyl of four to about twenty carbon atoms, cycloalkyl of from four to about eight carbon atoms, mono cycloalkyl substituted alkyl of from four to about twelve carbon atoms where cycloalkyl is about four to about eight carbon atoms, and mono to tetra alkyl substituted cycloalkyl of from four to about eight carbon atoms wherein alkyl is one to about four carbon atoms;

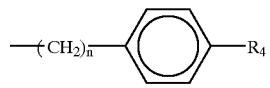

wherein n is 0 or 1 and $R_4$ is selected from the group consisting of hydrogen, alkyl of one to about twenty carbon atoms, cycloalkyl of from four to about eight carbon atoms, mono cycloalkyl substituted alkyl of from four to about twelve carbon atoms where cycloalkyl is about four to about eight carbon atoms, and mono to tetra alkyl substituted cycloalkyl of from four to about eight carbon atoms wherein alkyl is one to about four carbon atoms.

$R_3$ is selected from the group consisting of hydrogen and alkyl of three to eight carbon atoms with the provisio that when $R_2$ is at the 4 position then $R_3$ is at the 5 position and when $R_2$ is at the 5 position then $R_3$ is at the 4 position; and pharmaceutically acceptable salts thereof.

DETAILED DESCRIPTION OF THE INVENTION

The compounds of this invention are active against bacteria, particularly bacteria which are resistant to drugs and more particularly are very active against methicillin resistance bacteria such as members of the staphylococcus family, for example *staphylococcus aureus*. The active compounds of the invention inhibits the growth of the bacteria (bacteriostatic) and/or kill the bacteria (bactericidal).

The active compounds can be used as a disinfectant or in any other antibacterial compositions for example wherein it is the sole antibacterial active material or used in a combination with any other antibacterial compound wherein inhibition of bacteria is desirable or compound which promotes antibacterial activity. Examples of such other antibacterial active(s) include triclosan, triclocarbons, p-chloro-m-xylenol, thymol, benzethonium chloride, an antibiotic, and the like. The active compound(s) can be combined with any nontoxic to the host or surface compatible carrier to bring about the desired effect(s). Examples of such carrier(s) are water, alcohol, oils, glycols, surfactants and combination(s) thereof. Situations in which the active compound(s) can be administered are to inanimate surfaces which are in need of cleansing such as surgical instruments, floor(s), wall(s), glass area, plastic ware and the like in homes and particularly in settings wherein bacterial contamination is an issue such as nursing homes, assisted care living facilities, hospitals, bathrooms, kitchens and the like. Non-inanimate surfaces such as skin, hair, oral cavity, teeth, mucous membranes and the like can be treated through topical administration of a composition containing appropriate quantities of the active compound(s) such as solids, liquids, gels, aerosols, emulsions, suspensions, ointments, salves, lotions, creams, toothpaste, mouthrinse, mucoadhesive materials, and other delivery vehicles.

The antibacterial active compound(s) can be delivered systemically to mammals, particularly humans in any non-toxic pharmaceutically acceptable vehicle in a minimum effective dose or more to a pharmaceutically effective non-toxic or essentially nontoxic maximum. The compound(s) can be delivered orally, topically or parenterally. The active compounds are particularly useful for mammals who are in need of treatment for antibacterial compound resistant bacteria, more particularly methicillin resistant bacteria.

Examples of pharmaceutical dosage unit forms include pills, capsules, tablets, teaspoons, tablespoons, droppers, syringes and the like.

The quantities of active compound(s) which can be employed in the composition can vary from about 0.01 wt % to about 5 wt % of the composition for antibacterial treatment on an inanimate surface, desirably about 0.1 to about 2 and more desirably about 0.25 to about 1.0. For topical treatment of mammalian surfaces the quantity of active compound(s) which can be employed is from about 0.01 to about 1.0, desirably about 0.03 to about 0.5 and more desirably about 1 to about 0.35.

A particularly desirable method of treating inanimate or mammalian surfaces is using antibacterial effective amounts of the compounds of this invention in conjunction with cleansing effective amounts of a surfactant, particularly an anionic surfactant. For treatment of mammalian surfaces, it is preferable to use levels of a surfactant(s) which are above those level(s) used in a composition used in the oral cavity such as a toothpaste, gel, gum, powder, mouth wash and the like.

There must be at least one surfactant present in the composition. The surfactant can be anionic, nonionic, amphoteric, or cationic, preferably anionic. Soap, a long chain alkyl or alkenyl, branched or normal carboxylic acid salt such as sodium, potassium, ammonium or substituted ammonium salt can be present in the composition as an example of an anionic surfactant. Exemplary of long chain alkyl or alkenyl are from about 8 to about 22 carbon atoms in length, specifically about 10 to about 20 carbon atoms in length, more specifically alkyl and most specifically normal, or normal with little branching. Small quantities of olefinic bond(s) may be present in the predominantly alkyl sections, particularly if the source of the "alkyl" group is obtained from a natural product such as tallow, coconut oil and the like. Because of its potential harshness soap is not a preferred surfactant and can be omitted from the composition unless a soap-containing bar is employed or mildness increasing corrections are employed.

Other surfactants can be present in the composition in addition to or instead of soap. Examples of such surfactants are the anionic, amphoteric, nonionic and cationic surfactants. Examples of anionic surfactants include but are not limited to soaps, alkyl sulfates, anionic acyl sarcosinates, methyl acyl taurates, N-acyl glutamates, acyl isethionates, alkyl sulfosuccinates, alkyl phosphate esters, ethoxylated alkyl phosphate esters, trideceth sulfates, protein condensates, mixtures of ethoxylated alkyl sulfates and the like.

Alkyl chains for these surfactants are $C_8$–$C_{22}$, preferably $C_{10}$–$C_{18}$, more preferably $C_{12}$–$C_{14}$.

Anionic non-soap surfactants can be exemplified by the alkali metal salts of organic sulfate having in their molecular structure an alkyl radical containing from about 8 to about 22 carbon atoms and a sulfonic acid or sulfuric acid ester radical (included in the term alkyl is the alkyl portion of higher acyl radicals). Preferred are the sodium, ammonium, potassium or triethanolamine alkyl sulfates, especially those obtained by sulfating the higher alcohols ($C_8$–$C_{18}$ carbon atoms), sodium coconut oil fatty acid monoglyceride sulfates and sulfonates; sodium or potassium salts of sulfuric acid esters of the reaction product of 1 mole of a higher fatty alcohol (e.g., tallow or coconut oil alcohols) and 1 to 12 moles of ethylene oxide; sodium or potassium salts of alkyl phenol ethylene oxide ether sulfate with 1 to 10 units of ethylene oxide per molecule and in which the alkyl radicals contain from 8 to 12 carbon atoms, sodium alkyl glyceryl ether sulfonates; the reaction product of fatty acids having from 10 to 22 carbon atoms esterified with isethionic acid and neutralized with sodium hydroxide; water soluble salts of condensation products of fatty acids with sarcosine; and others known in the art.

Zwitterionic surfactants can be exemplified by those which can be broadly described as derivatives of aliphatic quaternary ammonium, phosphonium, and sulfonium compounds, in which the aliphatic radicals can be straight chain or branched and wherein one of the aliphatic substituents contains from about 8 to 18 carbon atoms and one contains an anionic water-solubilizing group, e.g., carboxy, sulfonate, sulfate, phosphate, or phosphonate. A general formula for these compounds is:

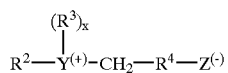

wherein $R^2$ contains an alkyl, alkenyl, or hydroxy alkyl radical of from about 8 to about 18 carbon atoms, from 0 to about 10 ethylene oxide moieties and from 0 to 1 glyceryl moiety; Y is selected from the group consisting of nitrogen, phosphorus, and sulfur atoms; R3 is an alkyl or monohydroxyalkyl group containing 1 to about 3 carbon atoms; X is 1 when Y is a sulfur atom and 2 when Y is a nitrogen or phosphorus atom, $R^4$ is an alkylene or hydroxyalkylene of from 0 to about 4 carbon atoms and Z is a radical selected from the group consisting of carboxylate, sulfonate, sulfate, phosphonate, and phosphate groups.

Examples include:

4-[N,N-di(2-hydroxyethyl)-N-octadecylammonio]-butane-1-carboxylate;

5-[S-3-hydroxypropyl-S-hexadecylsulfonio]-3 hydroxypentane-1-sulfate;

3-[P,P-P-diethyl-P 3,6,9 trioxatetradecyl-phosphonio]-2-hydroxypropane-1-phosphate;

3-[N,N-dipropyl-N-3 dodecoxy-2-hydroxypropylammonio]-propane-1-phosphonate;

3-(N,N-di-methyl-N-hexadecylammonio)propane-1-sulfonate;

3-(N,N-dimethyl-N-hexadecylammonio)-2-hydroxypropane-1-sulfonate;

4-(N,N-di(2-hydroxyethyl)-N-(2 hydroxydodecyl)ammonio]-butane-1-carboxylate;

3-[S-ethyl-S-(3-dodecoxy-2-hydroxypropyl)sulfonio]-propane-1-phosphate;

3-(P,P-dimethyl-P-dodecylphosphonio)-propane-1-phosphonate; and

5-[N,N-di(3-hydroxypropyl)-N-hexadecylammonio]-2-hydroxypentane-1-sulfate.

Examples of amphoteric surfactants which can be used in the compositions of the present invention are those which can be broadly described as derivatives of aliphatic secondary and tertiary amines in which the aliphatic radical can be straight chain or branched and wherein one of the aliphatic substituents contains from about 8 to about 18 carbon atoms and one contains an anionic water solubilizing group, e.g., carboxy, sulfonate, sulfate, phosphate, or phosphonate. Examples of compounds falling within this definition are sodium 3-dodecylaminopropionate, sodium 3-dodecylaminopropane sulfonate, N-alkyltaurines, such as the one prepared by reacting dodecylamine with sodium isethionate according to the teaching of U.S. Pat. No.

2,658,072, N-higher alkyl aspartic acids, such as those produced according to the teaching of U.S. Pat. No. 2,438,091, and the products sold under the trade name "Miranol" and described in U.S. Pat. No. 2,528,378. Other amphoterics such as betaines are also useful in the present composition.

Examples of betaines useful herein include the high alkyl betaines such as coco dimethyl carboxymethyl betaine, lauryl dimethyl carboxy-methyl betaine, lauryl dimethyl alpha-carboxyethyl betaine, cetyl dimethyl carboxymethyl betaine, lauryl bis-(2-hydroxyethyl)carboxy methyl betaine, stearyl bis-(2-hydroxypropyl) carboxymethyl betaine, oleyl dimethyl gamma-carboxypropyl betaine, lauryl bis-(2-hydro-xypropyl) alpha-carboxyethyl betaine, etc. The sulfobetaines may be represented by coco dimethyl sulfopropyl betaine, stearyl dimethyl sulfopropyl betaine, amido betaines, amidosulfobetaines, and the like.

Many cationic surfactants are known to the art. By way of example, the following may be mentioned:

stearyidimenthylbenzyl ammonium chloride;
dodecyltrimethylammonium chloride;
nonylbenzylethyldimethyl ammonium nitrate;
tetradecylpyridinium bromide;
laurylpyridinium chloride;
cetylpyridinium chloride
laurylpyridinium chloride;
laurylisoquinolium bromide;
ditallow(Hydrogenated)dimethyl ammonium chloride;
dilauryldimethyl ammonium chloride; and
stearalkonium chloride.

Additional cationic surfactants are disclosed in U.S. Pat. No. 4,303,543 see column 4, lines 58 and column 5, lines 1–42, incorporated herein by references. Also see CTFA Cosmetic Ingredient Dictionary, 4th Edition 1991, pages 509–514 for various long chain alkyl cationic surfactants; incorporated herein by references.

Nonionic surfactants can be broadly defined as compounds produced by the condensation of alkylene oxide groups (hydrophilic in nature) with an organic hydrophobic compound, which may be aliphatic or alkyl aromatic in nature. Examples of preferred classes of nonionic surfactants are:

1. The polyethylene oxide condensates of alkyl phenols, e.g., the condensation products of alkyl phenols having an alkyl group containing from about 6 to 12 carbon atoms in either a straight chain or branched chain configuration, with ethylene oxide, the said ethylene oxide being present in amounts equal to 10 to 60 moles of ethylene oxide per mole of alkyl phenol. The alkyl substituent in such compounds may be derived from polymerized propylene, diisobutylene, octane, or nonane, for example.

2. Those derived from the condensation of ethylene oxide with the product resulting from the reaction of propylene oxide and ethylene diamine products which may be varied in composition depending upon the balance between the hydrophobic and hydrophilic elements which is desired. For example, compounds containing from about 40% to about 80% polyoxyethylene by weight and having a molecular weight of from about 5,000 to about 11,000 resulting from the reaction of ethylene oxide groups with a hydrophobic base constituted of the reaction product of ethylene diamine and excess propylene oxide, said base having a molecular weight of the order of 2,500 to 3,000, are satisfactory.

3. The condensation product of aliphatic alcohols having from 8 to 18 carbon atoms, in either straight chain or branched chain configuration with ethylene oxide, e.g., a coconut alcohol ethylene oxide condensate having from 10 to 30 moles of ethylene oxide per mole of coconut alcohol, the coconut alcohol fraction having from 10 to 14 carbon atoms. Other ethylene oxide condensation products are ethoxylated fatty acid esters of polyhydric alcohols (e.g., Tween 20-polyoxyethylene (20) sorbitan monolaurate).

4. Long chain tertiary amine oxides corresponding to the following general formula:

wherein $R_1$ contains an alkyl, alkenyl or monohydroxy alkyl radical of from about 8 to about 18 carbon atoms, from 0 to about 10 ethylene oxide moieties, and from 0 to 1 glyceryl moiety, and, $R_2$ and $R_3$ contain from 1 to about 3 carbon atoms and from 0 to about 1 hydroxy group, e.g., methyl, ethyl, propyl, hydroxy ethyl, or hydroxy propyl radicals. The arrow in the formula is a conventional representation of a semipolar bond. Examples of amine oxides suitable for use in this invention include dimethyldodecylamine oxide, oleyl-di(2-hydroxyethyl) amine oxide, dimethyloctylamine oxide, dimethyldodecylamine oxide, dimethyltetradecylamine oxide, 3,6,9 trioxaheptadecyldiethylamine oxide, di(2-hydroxyethyl)-tetradecylamine oxide, 2-dodecoxyethyldimethylamine oxide, 3-dodecoxy-2-hydroxypropyldi(3-hydroxypropyl)amine oxide, dimethylhexadecyl-amine oxide.

5. Long chain tertiary phosphine oxides corresponding to the following general formula:

wherein R contains an alkyl, alkenyl or monohydroxyalkyl radical ranging from 8 to 20 carbon atoms in chain length, from 0 to about 10 ethylene oxide moieties and from 0 to 1 glyceryl moiety and R' and R" are each alkyl or monohydroxyalkyl groups containing from 1 to 3 carbon atoms. The arrow in the formula is a conventional representation of a semipolar bond. Examples of suitable phosphine oxides are: dodecyldimethylphosphine oxide, tetradecylmethylethylphosphine oxide, 3,6,9-trioxaoctadecyldimethylphosphine oxide, cetyldimethylphosphine oxide, 3-dodecoxy-2-hydroxypropyldi(2-hydroxyethyl) phosphine oxide stearyldimethylphosphine oxide, cetylethyl propylphosphine oxide, oleyldiethylphosphine oxide, dodecyldiethylphosphine oxide, tetradecyldiethylphosphine oxide, dodecyldipropylphosphine oxide, dodecyldi(hydroxymethyl)phosphine oxide, dodecyldi(2-hydroxyethyl)phosphine oxide, tetradecylmethyl-2-hydroxypropylphosphine oxide, oleyldimethylphosphine oxide, 2-hydroxydodecyldimethylphosphine oxide.

6. Long chain dialkyl sulfoxides containing one short chain alkyl or hydroxy alkyl radical of 1 to about 3 carbon atoms (usually methyl) and one long hydrophobic chain which contain alkyl, alkenyl, hydroxy alkyl, or keto alkyl radicals containing from about 8 to about 20 carbon atoms, from 0 to about 10 ethylene oxide moieties and from 0 to 1 glyceryl moiety. Examples include: octadecyl methyl sulfoxide, 2-ketotridecyl methyl sulfoxide, 3,6,9-trioxaoctadecyl 2-hydroxyethyl sulfoxide, dodecyl methyl sulfoxide, oleyl 3-hydroxypropyl sulfoxide, tetradecyl methyl sulfoxide, 3 methoxytridecylmethyl sulfoxide, 3-hydroxytridecyl methyl sulfoxide, 3-hydroxy-4-dodecoxybutyl methyl sulfoxide.

7. Alkylated polyglycosides wherein the alkyl group is from about 8 to about 20 carbon atoms, preferably about 10 to about 18 carbon atoms and the degree of polymerization of the glycoside is from about 1 to about 3, preferably about 1.3 to about 2.0.

When dosing a mammal systemically, the quantity of antibacterial compound is from about 0.01 to about 50, desirably about 0.1 to about 10 and more desirably about 0.02 to about 5. All doses are on the basis of mg/kg (body weight)/day and can be provided one to four times per day to the patient.

Studies showing the antibacterial activity of these compound(s), particularly the drug resistant, methicillin resistant antibacterial activity, are present as shown below.

Evaluation of Several Phenolic Antimicrobial Agents Against *Staphylococcus Aureus*

Experimental Method

Antimicrobial activity of several compounds was measured by determining the minimum inhibitory concentration (MIC). MIC is defined as the lowest concentration of an antimicrobial agent that will inhibit the growth of a microorganism and is usually expressed as ppm ($\mu$g/mL). MIC was determined by the Broth Dilution Method. To determine MIC a series of culture tubes was prepared, each tube containing the growth medium (Broth) with a decreasing concentration of the antimicrobial agent. The tubes were then inoculated with the test organism and incubated at 37° C. After incubation, tubes were visually examined for growth as indicated by turbidity. The lowest concentration that prevented visible growth is the MIC. MIC values for various compounds tested using *Staphylococcus Aureus* as the test organism are shown in Table 1.

TABLE 1

MIC Results For Several Phenols Against *Staphylococcus Aureus*

| Compound | MIC $\mu$g/mL |
| --- | --- |
| 2-t-butyl-5-(4-t-butylphenyl)-phenol (DTBBP) | <1.0 |
| 2-t-butyl-5-(4-t-butylcyclohexyl)-phenol | <10.0 |
| 2-t-butyl-4-cyclohexylphenol | <10.0 |
| 2-t-butyl-4-n-octylphenol | <10.0 |

Evaluation of DTBBP Against Drug Resistant Strains of *Staphylococcus Aureus*

Experimental Method

1. The following *Staphylococcus Aureus* isolates were tested:

TABLE 2

| Isolate | Results |
| --- | --- |
| SA22 | Resistant to methicillin, azithromycin, clarithromycin, erythromycin, ciprofloxacin, trovafloxacin) |
| SA76 | Resistant to methicillin, azithromycin, clarithromycin, erythromycin, ciprofloxacin) |
| SA100 | Resistant to methicillin only |
| SA6 | Susceptible to all drugs |

TABLE 2-continued

| Isolate | Results |
| --- | --- |
| SA124 | Susceptible |
| SA15 | Susceptible |

Grown overnight on blood plates. Colonies picked into 5 ml sterile water to a 0.5 MacFarland density. 50 $\mu$l into 5 ml M-H broth for a density of $10^6$/mL.

2. 2-t-butyl-5-(4-t-butylphenyl)-phenol (DTBBP) was dissolved in ethanol to a concentration of 1000 $\mu$g/mL. Higher concentrations could not be tested due to the formation of precipitate in the broth when higher concentrations were attempted.

3. 100 $\mu$l of the 32 $\mu$g/ml solution added to column 12 of the multiwell plates, 50 $\mu$l M—H broth to each of the other columns. 50 $\mu$l removed from 12 to 11 for 1:1 dilution, continued to column 2. 50 $\mu$l removed from column 2 and discarded. Column 1 contained no drug. To control for the amount of ethanol added to each well, additional wells were set up as described above without DTBBP but with the same amount of ethanol as the test wells.

4. 50 $\mu$l bacteria added to each well going from column 1 to column 12. All isolates run in duplicate with and without DTBBP.

5. Addition of 50 $\mu$l bacteria to 50 $\mu$l drug dilutes both 1:1 for a final bacterial density of $5\times10^5$/ml and drug concentrations of:
   0 $\mu$l
   0.016 $\mu$l
   0.032 $\mu$l
   0.062 $\mu$l
   0.125 $\mu$l
   0.25 $\mu$l
   0.5 $\mu$l
   1 $\mu$l
   2 $\mu$l
   4 $\mu$l
   8 $\mu$l
   8 $\mu$l 6. Incubated overnight at 37° C.

MIC Results for Antibiotic Resistant *Staphyloccus Aureus* Strains

TABLE 3

| Isolate | DTBBP MIC $\mu$g/mL (24 hr/48 hr) |
| --- | --- |
| SA22 | 2/2 |
| SA76 | 2/4 |
| SA100 | 4/4 |
| SA6 | 2/4 |
| SA15 | 2/4 |
| SA124 | 2/4 |

Example of substituents of the compounds are shown below.

Examples of $R_1$ substituents of the active compounds are isobutyl, tert butyl, isoamyl, 2,3-dimethyl butyl, isoeicosyl, isododecyl, 2,2,4-trimethylpentyl, 2-ethylhexyl, 2-ethyl-5-methyldecyl, isooctadecyl, cyclobutyl, cyclohexyl, cycloheptyl, 3-cyclohexyloctyl, 3-methylcyclopentyl, 2,4-diethylcycloheptyl.

Examples of $R_2$ substituents of the active compounds are all of the $R_1$ group illustratively exemplified above as well as phenyl, benzyl, p-methyl phenyl, p-methyl benzyl, p-ethyl phenyl, p-isopropyl benzyl, p-t-butyl phenyl, p-1,1,3-trimethyl butyl benzyl, p-cyclohexyl phenyl, p-methyl cyclohexyl benzyl, p-4-t-butylcyclohexyl phenyl.

$R_3$ substituents are hydrogen, methyl, ethyl, propyl and isopropyl.

Preferred compounds of the invention are 2-t-butyl-5-(4-t-butylphenyl)-phenol (DTBBP), 2-t-butyl-5-(4-t-butylcyclohexyl)-phenol, 2-t-butyl-4-cyclohexylphenol, 2-t-butyl-3-octyloxyphenol, 2-t-butyl-4-n-octylphenol.

Examples of pharmaceutically acceptable salts of the phenolic compounds of this invention include alkali metal salts such as sodium and potassium; alkaline earth metal salts such as magnesium and calcium; strontium, amine salts such as ammonium, tetramethyl ammonium, triethanolamine, zinc; and the like.

Exemplary compositions of the invention are shown below.

EXAMPLE 1

Hand Cleansing Composition

| Ingredient | Wt % |
|---|---|
| 2-octyl-4-cyclohexylphenol | 0.3 |
| Propylene glycol | 3.0 |
| Lauramine oxide (30% active) | 5.0 |
| Hydroxyethyl cellulose | 0.7 |
| PH | 5.5 |
| Water | QS |
| TOTAL | 100 |

EXAMPLE 2

Dilutable Surface Cleaning Composition

| Ingredient | Wt % |
|---|---|
| 2-t-butyl-4-(4-t-butylbenzyl)-phenol | 14.0 |
| N-methylpyrrolidone | 9.7 |
| N-octylpyrrolidone | 14.1 |
| Nonyl phenol ethoxylated alcohol with 9 EOs | 14.0 |
| Sodium dodecyl sulfate | 14.0 |
| Water | QS |
| TOTAL | 100 |

Such a composition can be bucket dilutable to 10–200/l in water to make a stable cleaning solution.

EXAMPLE 3

Hydrophilic Ointment (1% DTBBP)

| Ingredient | Wt % |
|---|---|
| 2-t-butyl-5-(4-t-butylphenyl)-phenol | 1.0 |
| Methyl paraben | 0.025 |
| Propyl paraben | 0.015 |
| Sodium dodecyl sulfate | 0.1 |
| Propylene glycol | 12.0 |
| Stearyl alcohol | 25.0 |
| White petrolatum | 25.0 |
| Purified Water | QS (QS) |
| TOTAL | 100 |

EXAMPLE 4

Hydrophobic Ointment

| Ingredient | Wt % |
|---|---|
| 2-t-butyl-5-(4-t-butylphenyl)-phenol | 1 |
| White wax | 5 |
| White petrolatum | QS |
| TOTAL | 100 |

EXAMPLE 5

Body Wash With Anionic Surfactant

| Ingredient | Wt % |
|---|---|
| Cocoamidyl Propyl Betaine | 10 |
| Sodium Laureth Sulfate 2EtO | 9.3 |
| Decyl Glucoside | 2.3 |
| Tetrasodium EDTA | 0.08 |
| Polyquaternium-7 | 0.2 |
| Fragrance | 1.0 |
| 2-Cyclohexyl-4-tert-Octyl Phenol | 0.3 |
| Salt (NaCl) | 0.6 |
| Citric Acid | 0.6 |
| D.I. Water | QS |
| TOTAL | 100.0 |

EXAMPLE 6

Aerosol For Hard Surface Cleansing

| Ingredient | Wt % |
|---|---|
| Cocoamidylpropy. Betaine | 3 |
| Denatured Ethanol (94%) | 1 |
| Formalin | 1 |
| Fragrance | 0.3 |
| $C_{9-11}$ Alcohol Ethoxylate (EO5-8) | 1.6 |
| Propylene Glycol-N-Butyl Ether | 3 |
| 2-t-Butyl-4-Cyclohexyl Phenol | 0.3 |
| D.I. Water | QS |
| TOTAL | 100 |

EXAMPLE 7

Hand And Face Wash With Anionic Surfactant Polyquat System

| Ingredient | Wt % |
|---|---|
| C12–C14 alcohol-EO (1.0–2.0) Sulfate (Na salt) | 8 |
| Cocoamidopropyl betaine | 10 |
| Alklyl Polyglycosine (APG-600) | 1.2 |
| Polyquaternium-7 | 0.2 |
| 2-t-butyl-4-(4-tbutylbenzyl)-phenol | 0.3 |
| Fragrance | 0.4 |
| Citric Acid | 0.04 |
| Dibromo-Dicyano Butane 10% in DPG | 0.3 |
| Water | QS |
| TOTAL | 100.0 |

The pH of the compositions having the active compounds can range from about 5 to about 10, desirably about 6 to about 8.

What is claimed is:
1. A composition comprising:
(a) at least about 5 wt. % of a surfactant or mixture thereof; and

(b) an antibacterial effective amount of a compound of at least minimum effectiveness against methicillin drug resistant bacteria, said compound of the formula:

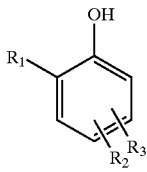

wherein $R_1$ is selected from the group consisting of branched alkyl of four to about twenty carbon atoms, cycloalkyl of from four to about eight carbon atoms, mono cycloalkyl substituted alkyl of from four to about twelve carbon atoms where cycloalkyl is about four to about eight carbon atoms, and mono to tetra alkyl substituted cycloalkyl of from four to about eight carbon atoms wherein alkyl is one to about four carbon atoms;

$R_2$ is at the 4 or 5 position and is selected from the group consisting of branched alkyl of four to about twenty carbon atoms, cycloalkyl of from four to about eight carbon atoms, mono cycloalkyl substituted alkyl of from four to about twelve carbon atoms where cycloalkyl is about four to about eight carbon atoms, and mono to tetra alkyl substituted cycloalkyl of from four to about eight carbon atoms wherein alkyl is one to about four carbon atoms;

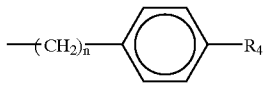

wherein n is 0 or 1 and $R_4$ is selected from the group consisting of hydrogen, alkyl of one to twenty carbon atoms, cycloalkyl of four to about eight carbon atoms, and mono to tetra alkyl substituted cycloalkyl of from four to about eight carbon atoms wherein alkyl is one to about four carbon atoms;

$R_3$ is selected from the group consisting of hydrogen and alkyl of one to three carbon atoms with the proviso that when $R_2$ is at the 4 position then $R_3$ is at the 5 position and when $R_2$ is at the 5 position then $R_3$ is at the 4 position; and pharmaceutically acceptable salts thereof.

2. A method for inhibiting drug resistant bacteria which comprises administering to a host or surface in need of said treatment a composition comprising a carrier and an antibacterially effective amount against methicillin drug resistant bacteria of a compound or a mixture of compounds of the formula:

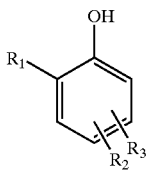

wherein
$R_1$ is selected from the group consisting of branched alkyl of four to about twenty carbon atoms, cycloalkyl of from four to about eight carbon atoms, mono cycloalkyl substituted alkyl of from four to about twelve carbon atoms where cycloalkyl is about four to about eight carbon atoms, and partially to fully alkyl substituted cycloalkyl of from four to about eight carbon atoms wherein alkyl is one to about four carbon atoms;

$R_2$ is at the 4 or 5 position and is selected from the group consisting of branched alkyl of four to about twenty carbon atoms, cycloalkyl of from four to about eight carbon atoms, mono cycloalkyl substituted alkyl of from four to about twelve carbon atoms where cycloalkyl is about four to about eight carbon atoms, and mono to tetra alkyl substituted cycloalkyl of from four to about eight carbon atoms wherein alkyl is one to about four carbon atoms;

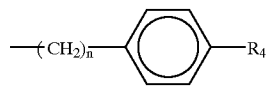

wherein n is 0 or 1 and $R_4$ is selected from the group consisting of hydrogen, alkyl of one to about twenty carbon atoms, cycloalkyl of from four to about eight carbon atoms, mono cycloalkyl substituted alkyl of from four to about twelve carbon atoms where cycloalkyl is about four to about eight carbon atoms, and mono to tetra alkyl substituted cycloalkyl of from four to about eight carbon atoms wherein alkyl is one to about four carbon atoms;

$R_3$ is selected from the group consisting of hydrogen and alkyl of three to eight carbon atoms with the proviso that when $R_2$ is at the 4 position then $R_3$ is at the 5 position and when $R_2$ is at the 5 position then $R_3$ is at the 4 position; and pharmaceutically acceptable salts thereof.

3. The method in accordance with claim 2 wherein the drug resistant bacterial is *staphylococcus aureus*.

4. The method in accordance with claim 3 wherein the compound is selected from the group consisting of 2-t-butyl-5-(4-t-butylphenyl)-phenol (DTBBP), 2-t-butyl-5-(4-t-butylcyclohexyl)-phenol, 2-t-butyl-4-cyclohexylphenol, 2-t-butyl-3-octyloxyphenol, 2-t-butyl-4-n-octylphenol and mixtures thereof.

5. The method in accordance with claim 2 wherein the composition is administered topically to a host or a surface.

6. The method in accordance with claim 5 wherein there is a skin cleansing or surface cleansing amount of surfactant or mixture thereof in the composition.

7. The method in accordance with claim 6 wherein the surfactant or mixture thereof is at least 5 wt % of the formulation.

8. The method in accordance with claim 2 wherein the composition is systematically administered to a host in need of said treatment.

9. The method in accordance with claim 5 wherein the composition is administered to a host.

10. The method in accordance with claim 5 wherein the composition is administered to a surface.

* * * * *